US011077264B2

(12) United States Patent
Qiu

(10) Patent No.: US 11,077,264 B2
(45) Date of Patent: Aug. 3, 2021

(54) ELECTRONIC CIGARETTE

(71) Applicant: Joyetech Europe Holding GmbH, Zug (CH)

(72) Inventor: Weihua Qiu, Jiangsu (CN)

(73) Assignee: JOYETECH EUROPE HOLDING GMBH, Zug (CH)

( * ) Notice: Subject to any disclaimer, the term of this patent is extended or adjusted under 35 U.S.C. 154(b) by 267 days.

(21) Appl. No.: 16/277,564

(22) Filed: Feb. 15, 2019

(65) Prior Publication Data

US 2019/0174831 A1 Jun. 13, 2019

Related U.S. Application Data

(63) Continuation-in-part of application No. PCT/CN2016/109532, filed on Dec. 12, 2016.

(30) Foreign Application Priority Data

Aug. 15, 2016 (CN) .......................... 201610667446.9

(51) Int. Cl.
*H01R 13/62* (2006.01)
*A61M 15/06* (2006.01)
(Continued)

(52) U.S. Cl.
CPC ............. *A61M 15/06* (2013.01); *A24F 40/48* (2020.01); *A24F 40/50* (2020.01); *A24F 40/60* (2020.01); *A61M 11/042* (2014.02); *A24F 15/015* (2020.01); *A24F 40/10* (2020.01); *A61M 11/007* (2014.02); *A61M 15/0066* (2014.02); *A61M 2016/0021* (2013.01); *A61M 2016/0033* (2013.01); *A61M 2205/103* (2013.01);
(Continued)

(58) Field of Classification Search
CPC ..... A24F 47/008; A24F 47/00; A61M 11/042; A61M 11/007; A61M 15/06; A61M 15/0066; A61M 2016/0021; A61M 2016/0033; A61M 2205/103; A61M 2205/3334
USPC ......................................... 131/273, 329–330
See application file for complete search history.

(56) References Cited

U.S. PATENT DOCUMENTS 8,991,402 B2 * 3/2015 Bowen ................. A61M 11/047
131/194
2009/0151717 A1 6/2009 Bowen et al.

FOREIGN PATENT DOCUMENTS

| CN | 202059988 U | 12/2011 |
| CN | 203851814 U | 10/2014 |
| CN | 203866012 U | 10/2014 |
| CN | 204104825 U | 1/2015 |

(Continued)

*Primary Examiner* — Khiem M Nguyen
(74) *Attorney, Agent, or Firm* — Novick, Kim & Lee, PLLC; Allen Xue

(57) ABSTRACT

An electronic cigarette includes a liquid storage device a liquid storage chamber, an atomizing device comprising an atomizing chamber, a controller, and a driving mechanism. The driving mechanism is electrically connected to the controller. When the controller controls the liquid intake of the electronic cigarette, the controller controls the driving mechanism to drive the e-cigarette liquid in the liquid storage chamber to enter the atomizing chamber, thereby realizing the control of the amount of the e-cigarette liquid in the atomizing device. In use, the electronic cigarette is provided with a proper amount of e-cigarette liquid in the atomizing device, and there is no dry burning or liquid leakage due to insufficient atomization.

18 Claims, 10 Drawing Sheets

(51) Int. Cl.
  *A61M 11/04* (2006.01)
  *A24F 40/48* (2020.01)
  *A24F 40/50* (2020.01)
  *A24F 40/60* (2020.01)
  *A61M 16/00* (2006.01)
  *A61M 15/00* (2006.01)
  *A61M 11/00* (2006.01)
  *A24F 15/015* (2020.01)
  *A24F 40/10* (2020.01)

(52) U.S. Cl.
  CPC ............... *A61M 2205/3334* (2013.01); *A61M 2205/3389* (2013.01); *A61M 2205/505* (2013.01); *A61M 2205/8206* (2013.01); *A61M 2209/045* (2013.01)

(56) References Cited

FOREIGN PATENT DOCUMENTS

| | | |
|---|---|---|
| CN | 204146331 A | 2/2015 |
| CN | 204377920 U | 6/2015 |
| CN | 104770898 A | 7/2015 |
| CN | 204519371 U | 8/2015 |
| CN | 104872820 A | 9/2015 |
| CN | 204930386 U | 1/2016 |
| CN | 105520197 A | 4/2016 |
| CN | 105768224 A | 7/2016 |
| CN | 106108121 A | 11/2016 |
| CN | 205947127 U | 2/2017 |
| EP | 2047880 A1 | 4/2009 |
| GB | 2524856 A | 10/2015 |
| KR | 10-1186229 B1 | 9/2012 |
| WO | 2017108394 A1 | 6/2017 |

\* cited by examiner

ELECTRONIC CIGARETTE

FIELD

The present disclosure relates to the field of electronic cigarette technology, and in particular, to an electronic cigarette with less dry burning and liquid leakage problems.

BACKGROUND

Most electronic cigarettes on the market use fiber rope or composite cotton to achieve oil guiding. When the user uses the electronic cigarette, it is easier to burn fiber rope or cotton due to less electronic cigarette liquid ("e-cigarette liquid" or "liquid") infiltrated on the liquid guiding member. When dry burning, the fiber rope or composite cotton is directly heated by the heating wire to emit burnt smoke, which is unpleasant and harmful to the body, also affects the taste of smoking. When there is a large amount of e-cigarette liquid infiltrated on the liquid guiding element and it is too late to be consumed, there is a risk of liquid leakage. Leakage and dry burning are common problems of current electronic cigarettes.

SUMMARY

The present disclosure provides an electronic cigarette with less dry burning and liquid leakage problems.

An electronic cigarette includes a liquid storage device a liquid storage chamber, an atomizing device comprising an atomizing chamber, a controller, and a driving mechanism, the liquid storage device includes a liquid storage chamber, the atomizing device includes an atomizing chamber, the driving mechanism is electrically connected to the controller is and coupled controlled by the controller, when the controller controls the liquid intake of the electronic cigarette, the controller controls the driving mechanism to drive the e-cigarette liquid in the liquid storage chamber to enter the atomizing chamber.

In one embodiment, after the end of the smoking, the controller controls the driving mechanism to drive the residual e-cigarette liquid in the atomization chamber to return to the liquid storage chamber.

In one embodiment, the electronic cigarette further includes a communication groove in communication with the liquid storage chamber, the atomizing device further includes an a liquid inlet, the atomizing chamber is in communication with liquid storage chamber through the liquid inlet, the driving mechanism includes a driving motor, a screw rod and a slider, the screw rod and the slider are disposed in the communication groove, the driving motor is disposed on the side of the communication groove away from the liquid storage chamber, the slider is connected to the screw rod; driven by the driving motor the lead screw drives the slider to move in a direction close to the liquid storage chamber or in a direction away from the liquid storage chamber.

In one embodiment, the slider is slidably connected to the screw rod; when the driving motor rotates, the screw rod is driven to rotate and drives slider to slide in a direction close to the liquid storage chamber or to slide away from the liquid storage chamber; or, the slider is disposed at one end of the screw rod near the liquid storage chamber, the screw rod is driven by the driving motor to make a telescopic motion and drives the slider to move in the direction close to or away from the liquid storage cavity in the communication groove.

In one embodiment, the controller includes a control switch and a control board, the control switch is signally connected to the control board, the driving mechanism is electrically connected to the control board and is coupled controlled by the control board, the controller further includes an input device, the input device is signally connected to the control board, the input device is configured for inputting desired operating temperature/operating power/operating voltage to the control board, the input device is a touch display or a touch switch, the control board is preset with a corresponding relationship between the rotational speed of the driving motor and the operating temperature/operating power/operating voltage of the atomizing device.

In one embodiment, the controller includes a control switch and a control board, the control switch is signally connected to the control board, the driving mechanism is electrically connected to the control board and is coupled controlled by the control board, the control switch is an airflow sensor configured to detect the flow velocity of the airflow when the user smoking, the control board is preset with a corresponding relationship between the rotational speed of the driving motor and the operating temperature/operating power/operating voltage of the atomizing device.

In one embodiment, the liquid storage device includes a liquid inlet tube, a first end of the liquid inlet tube is in communication with the atomizing chamber, a second end of the liquid inlet tube is in communication with the liquid storage chamber, the controller controls the driving mechanism to drive the e-cigarette liquid in the liquid storage chamber into the atomization chamber through the liquid inlet tube.

In one embodiment, the driving mechanism includes a piston, a connecting member and a driving motor, the piston is located in the liquid storage chamber, the piston divides the liquid storage chamber into a cavity and a communication chamber, the communication chamber is in communication with the atomizing chamber through the liquid inlet tube, the connecting member is connected between the piston and the driving motor, the connecting member drives the piston to move toward the communication chamber under the action of the driving motor.

In one embodiment, the second end of liquid inlet tube passes through the cavity and the piston in sequence, the second end of the inlet tube is inserted into the communication chamber.

In one embodiment, the liquid storage device further includes a connecting tube disposed between the communication chamber and the liquid inlet tube, the communication chamber is in communication with the liquid inlet tube through the connecting tube.

In one embodiment, the connecting member includes a screw, a slider, a rail and a connecting rod, the lead screw is connected to the driving motor, the screw rod extends through the slider, the slider is slidably connected to the guide rail, one end of the connecting rod is fixedly connected to the slider, and the other end of the connecting rod is fixedly connected to the piston.

In one embodiment, the electronic cigarette includes a liquid level detecting device, the liquid level detecting device disposed in the liquid storage chamber, the electronic cigarette further includes a display screen, the liquid level detecting device is electrically connected to the display screen.

In one embodiment, the electronic cigarette further includes a housing, the liquid storage chamber is located in the housing, a liquid inlet is defined at the bottom of the liquid storage chamber, an opening is provided at the bottom wall of the housing corresponding to the liquid inlet, the electronic cigarette further includes a liquid injection assembly for covering the opening.

In one embodiment, when the liquid inlet is in communication with the liquid bottle, the drive motor is controlled to be reversed by the controller, the connecting member drives the piston to move toward the cavity to achieve automatic liquid injection.

In one embodiment, the liquid injection assembly includes a mounting member, an opening and closing member, and a telescopic liquid filling tube, the telescopic liquid injection tube is fixedly connected to the mounting member, the opening and closing member is rotatably connected to the mounting member, the mounting member is connected to the housing, the upper port of the telescopic infusion tube is sealing connected to the opening, the opening and closing member includes an open state and a closed state, when the opening and closing member is in the closed state, the lower port of the telescopic liquid filling tube is sealing abutted against the opening and closing member.

In one embodiment, the telescopic liquid injection tube includes a first tube and a multi-section telescopic tube, the first tube is fixedly connected to the mounting member, the two adjacent telescopic tubes are nested and connected.

In one embodiment, a single-conducting portion is located in the liquid inlet tube, the single-conducting portion prevents the e-cigarette liquid in the atomizing chamber from flowing back into the liquid storage chamber when the e-cigarette liquid is injected into the liquid storage chamber.

In one embodiment, the controller includes a control board, a liquid inlet control switch and/or a liquid injection control switch, the liquid inlet control switch and/or the liquid injection control switch are signally connected to the control board, the driving mechanism is coupled controlled by the control board, when the liquid inlet control switch or the liquid injection control switch is turned on, the control board is triggered and the control board controls the movement of the driving mechanism.

In one embodiment, the controller further includes a liquid injection amount control portion and/or a liquid intake amount control portion, the liquid injection amount control portion and/or liquid intake amount control portion is signally connected to the control board, the liquid injection amount control portion is mechanical, the liquid injection amount control portion includes a plurality of gear positions, each gear position corresponds to the amount of liquid injection each time; or, the liquid injection amount control portion is a touch screen typed liquid injection amount control portion, the touch screen typed injection amount control portion is configured to set liquid injection amount value, the liquid amount control portion is mechanical, the liquid intake amount control unit includes a plurality of gear positions, each of which corresponds to a liquid intake amount each time, or the liquid intake amount control portion is a touch screen type, the touch screen typed liquid intake amount control portion is configured to set the amount of liquid intake.

In one embodiment, the controller further includes an atomization control switch, the liquid inlet control switch and the atomization control switch is controlled separately or coupled controlled.

The beneficial effects of the device are:

In the electronic cigarette of the present disclosures, the controller controls the driving mechanism to drive the e-cigarette liquid in the liquid storage chamber into the atomizing device, thereby realizing the control of the amount of the e-cigarette liquid in the atomizing device. That is to say, during the user smoking, the electronic cigarette can always provide with a proper amount of e-cigarette liquid in the atomizing device, and there is no dry burning or liquid leakage caused by insufficient atomization.

Figure 1:
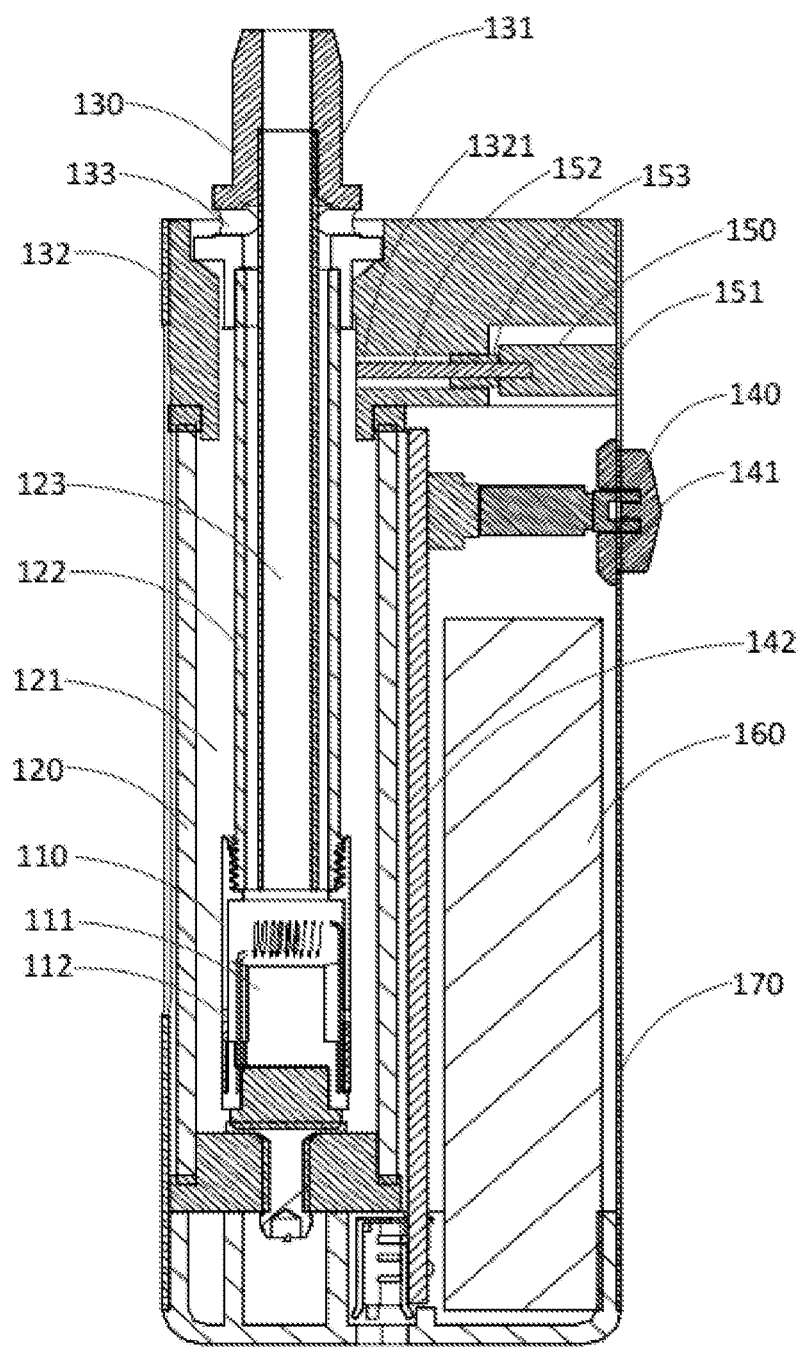
FIG. 1 is a cross-sectional view of an electronic cigarette according to the first embodiment of the present disclosure.

The following table list various components and reference numerals thereof.

| | |
|---|---|
| atomizing device 110, 210 | atomizing chamber 111 |
| liquid storage chamber 121, 220 | vent pipe 122 |
| mouthpiece 131 | mouthpiece connector 132 |
| air intake hole 133 | controller 140 |
| airflow sensor 141b | screw rod 152, 2441 |
| driving motor 151 | cavity 220b |
| housing 170, 250 | first end 222a |
| communication chamber 220a | piston 240 |
| liquid inlet tube 222 | guide rail 2443 |
| control board 232, 142 | battery 252 |
| slider 2442, 153 | telescopic liquid injection tube 264 |
| observation window 2501 | liquid storage device 120 |
| opening and closing member 262 | mouthpiece assembly 130 |
| connecting tube 270 | airflow detection channel 1322 |
| liquid inlet 112 | key switch 141a |
| air outlet pipe 123 | driving mechanism 150 |
| communication groove 1321 | battery 160 |
| control switch 141 | Injection hole 2202 |
| input device 143 | liquid inlet control switch 230 |
| atomizing chamber 211 | groove 2601 |
| convex ring 2201 | telescopic tube 2642 |
| second end 222b | mounting member 260 |
| driving motor 242 | first tube 2641 |
| connecting rod 2445 | |

DETAILED DESCRIPTION OF PREFERRED EMBODIMENTS

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "comprising," when utilized, means "including, but not necessarily limited to"; it specifically indicates open-ended inclusion or membership in the so-described combination, group, series and the like.

When a feature or element is herein referred to as being "on" another feature or element, it can be directly on the other feature or element or intervening features and/or elements may also be present.

Terminology used herein is for the purpose of describing particular embodiments only and is not intended to be limiting of the disclosure. As used herein, the term "and/or" includes any and all combinations of one or more of the associated listed items and may be abbreviated as "/".

Referring to FIG. 1, the electronic cigarette in the first embodiment includes a liquid storage device 120, an atomizing device 110, a controller 140, and a driving mechanism 150. The liquid storage device 120 includes a liquid storage chamber 121. The atomizing device 110 is received in the liquid storage chamber 121. The driving mechanism 150 is electrically connected to and is coupled controlled by the controller 140. The controller 140 controls the amount of the e-cigarette liquid in the liquid storage chamber 121 to enter and exit the atomizing device 110. Specifically, the controller 140 can control the amount of e-cigarette liquid driven by the driving mechanism 150 into and out of the atomizing device 110. As long as the controller 140 controls the entry and exit of the electronic cigarette, the driving mechanism 150 drives the e-cigarette liquid in the liquid storage chamber 121 to enter and exit the atomizing device 110, thereby realizing the control of the amount of the liquid in the atomizing device 110. Thereby, when the user smokes electronic cigarette, there is an appropriate amount of e-cigarette liquid in the atomizing device 110, there is no dry burning and liquid leakage due to insufficient atomization. After smoking, the e-cigarette liquid in the atomizing device 110 returns to the liquid storage chamber 121, thereby reducing the possibility of leakage of residual e-cigarette liquid, and ensuring the taste of the user when smoking again.

The atomizing device 110 includes an atomizing chamber 111 and a liquid inlet 112 in communication with the atomizing chamber 111. The atomizing device 110 is in communication with the liquid storage chamber 121 through the liquid inlet 112. That is, when the electronic cigarette is in use, the liquid smoke enters the atomizing chamber 111 of the atomizing device 110 from the liquid storage chamber 121 through the liquid inlet 112 under the action of the driving mechanism 150. When not in use, the liquid can also be returned to the liquid storage chamber 121 by the atomizing chamber 111 under the action of the driving mechanism 150.

The electronic cigarette further includes a mouthpiece assembly 130, the mouthpiece assembly 130 includes a mouthpiece connector 132 and a mouthpiece 131 disposed on the mouthpiece connector 132. The mouthpiece connector 132 is disposed on the liquid storage device 120. A communication groove 1321 in communication with the liquid storage chamber 121 is disposed in the mouthpiece connector 132. The mouthpiece connector 132 is further provided with an air inlet hole 133 for air to enter the atomizing chamber 111.

A vent pipe 122 is disposed in the liquid storage chamber 121. The vent pipe 122 has a cylindrical structure, one end of the vent pipe 122 is in communication with the atomizing device 110, the other end of the vent pipe 122 is communication with the air inlet hole 133. An air outlet pipe 123 is disposed in the vent pipe 122. One end of the air outlet pipe 123 is in communication with the atomizing device 110, and the opposite end of the air outlet pipe 123 is in communication with the mouthpiece 131. The outside air enters the gap between the vent pipe 122 and the air outlet pipe 123 through the air inlet hole 133, flows to the top end of the atomizing device 110 and mixes with the smoke formed by the atomization, and then flows out through the air outlet pipe 123 and is inhaled by the user at the mouthpiece 131.

The driving mechanism 150 includes a driving motor 151, a screw rod 152 and a slider 153. The screw rod 152 is connected to the driving motor 151, the slider 153 is slidably connected to the screw rod 152. Thus, the screw rod 152 is driven to rotate when the driving motor 151 rotates, thereby driving the slider 153 to move on the screw rod 152. The screw rod 152 and the slider 153 are disposed in the communication groove 1321, the driving motor 151 is disposed on the side of the communication groove 1321 away from the liquid storage chamber 121. The slider 153 can reciprocate in the communication groove 1321 under the driving of the screw rod 152 to adjust the pressure in the liquid storage chamber 121. That is, when the slider 153 moves toward the liquid storage chamber 121, the pressure inside of the liquid storage chamber 121 increases and the amount of e-cigarette liquid in the liquid storage chamber 121 enters the atomizing chamber 111 increases. When the slider 153 moves away from the liquid storage chamber 121, the pressure in the liquid storage chamber 121 decreases, and the e-cigarette liquid in the atomizing chamber 111 returns to the liquid storage chamber 121. The moving speed of the slider 153 also affects the flow rate of the liquid. Taking the slider 153 moving toward the liquid storage chamber 121 as an example, the slider 153 moves fast, and the flow rate of the liquid into the atomizing chamber 111 is high, and conversely, the flow rate of the liquid into the atomizing chamber 111 is low. In addition, by adopting the rod screw, precise quantitative e-cigarette liquid feeding can be realized. Specifically, when the screw rod 152 is rotated one turn, the slider 153 can be linearly moved by a certain distance, and quantitative supply of liquid smoke can be achieved. It can be understood that, the driving motor 151 can adopt any form of motor, when the driving motor 151 is a stepping motor or a servo motor, the movement of the slider 153 can be controlled more precisely.

It is to be understood that, in another embodiment not shown, the cross section of the communication groove 1321 is circular, the slider 153 is disposed at one end of the screw rod 152 near the liquid storage chamber 121. The screw rod 152 is driven by the driving motor 151 to make a telescopic motion and drives the slider 153 to move toward or away from the liquid storage chamber 121 in the communication groove 1321. It can be understood that, the driving motor 151 can be replaced with a cylinder. It can be understood that, the cross section of the communication groove 1321 can also be a non-circular structure such as a rectangle, an ellipse or a diamond. In order to ensure a smoother movement of the slider 153 and the screw rod 152, the slider 153 is also selected to have a shape matching the communication groove 1321, such as a rectangle, an ellipse, a diamond, or the like.

Figure 2:
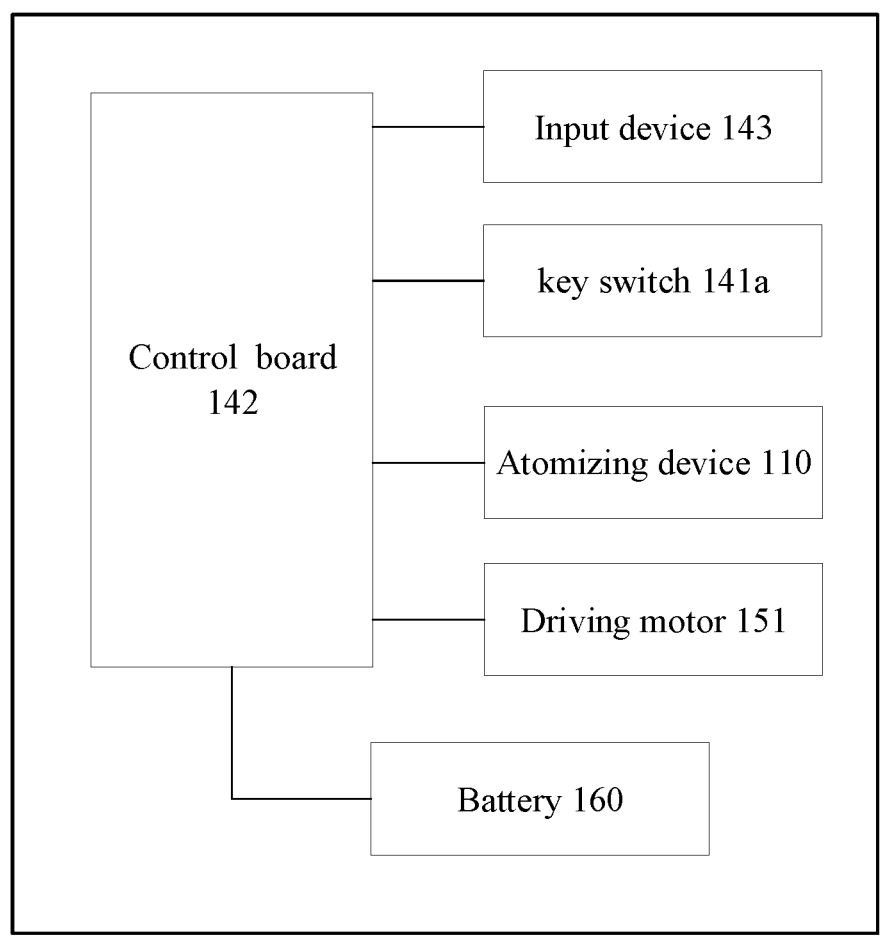
FIG. 2 is a block diagram of the first embodiment of the present disclosure.

Referring to FIG. 2, further, the controller 140 includes a control switch 141, a control board 142, and an input device 143. In one embodiment, the control switch 141 is a key switch 141a, the input device 143 is a touch display screen, the key switch 141a and the input device 143 are separately connected to the control board 142. The input device 143 is configured for inputting data of the atomizing device 110 into the control board 142, such as working temperature, operating power and operating voltage, etc. The control board 142 is pre-configured with a corresponding relationship between the rotational speed of the driving motor 151 and the operating temperature/operating power/operating voltage of the atomizing device 110. The driving mechanism 150 is electrically connected to and controlled by the control board 142, when the key switch 141a is turned on, the control board 142 is triggered and controls the movement of the driving mechanism 150. The user inputs a desired operating temperature/operating power/operating voltage into the control board 142 through the input device 143. The control board 142 controls the operating temperature/operating power/operating voltage of the atomizing device 110 according to the input data. The control board 142 also controls the rotation speed of the driving motor 151 according to the input data and the corresponding relationship between the rotation speed of the driving motor 151 pre-configured therein and the operating temperature/operating power/operating voltage of the atomizing device 110, thereby realizing the control of the liquid intake amount.

It can be understood that the control switch 141 can control the liquid storage chamber 121 to feed into the atomizing chamber 111, and can also control the e-cigarette liquid in the atomizing chamber 111 to be sucked back into the liquid storage chamber 121, and can also control the opening and closing of the atomizing device 110. The input device 143 can be a touch display, the control switch 141 can be a touch switch.

The electronic cigarette further includes a battery 160 and a housing 170. The liquid storage device 120, the atomizing device 110, the driving mechanism 150 and the battery 160 are all received in the housing 170. The atomizing device 110, the controller 140, and the driving mechanism 150 are electrically connected to the battery 160, respectively. To facilitate the observation of the e-cigarette liquid in the liquid storage chamber 121, the material of the peripheral wall of the liquid storage chamber 121 may be made of a transparent material such as glass or transparent resin. An observation window (not shown) is disposed on the housing 170, the amount of the liquid in the liquid storage chamber 121 can be visually observed through the observation window.

In the embodiment, when the electronic cigarette is in use, the user inputs a desired working temperature/operating power/operating voltage through the touch display screen, and the touch display screen transmits the data to the control board 142. The control board 142 is triggered by the user through the key switch 141a, the control board 142 matches the data received from the touch display screen with the preset pre-configured with a corresponding relationship between the rotational speed of the driving motor 151 and the operating temperature/operating power/operating voltage of the atomizing device 110, and controls the driving motor 151 to rotate. In the initial state, the slider 153 stays on a side of the communication groove 1321 away from the liquid storage chamber 121. When the desired operating temperature/operating power/operating voltage is large, the atomizing device 110 has a large atomization rate, the driving motor 151 rotates faster, and the driving slider 153 moves rapidly toward the liquid storage chamber 121, the liquid in the liquid storage chamber 121 quickly enters the atomizing chamber 111, which satisfies the requirement of the atomizing device 110 for the amount of e-cigarette liquid, and avoids dry burning. When the desired operating temperature/operating power/operating voltage is small, the atomization rate of the atomizing device 110 is small, the driving motor 151 rotates at a low speed or does not rotate, the driving slider 153 moves slowly or does not move in a direction close to the liquid storage chamber 121, the e-cigarette liquid in the liquid storage chamber 121 slowly enters the atomizing chamber 111, which satisfies the requirement of the atomizing device 110 for the amount of e-cigarette liquid, avoids excessive e-cigarette liquid and insufficient atomization. After the end of the smoking, the driving motor 151 drives the slider 153 to move away from the liquid storage chamber 121, that is, the initial state is restored. At this time, the pressure in the liquid storage chamber 121 is reduced, the excess e-cigarette liquid in the atomizing chamber 111 is returned to the liquid storage chamber 121 under the action of air pressure, the residual of the e-cigarette liquid in the atomizing chamber 111 is avoided. This can reduce the possibility of leakage of e-cigarette liquid when the electronic cigarette is not used, and ensure that the user does not inhale the residual e-cigarette liquid when the user smokes again, ensuring the taste of smoking.

The Second Embodiment

Figure 3:
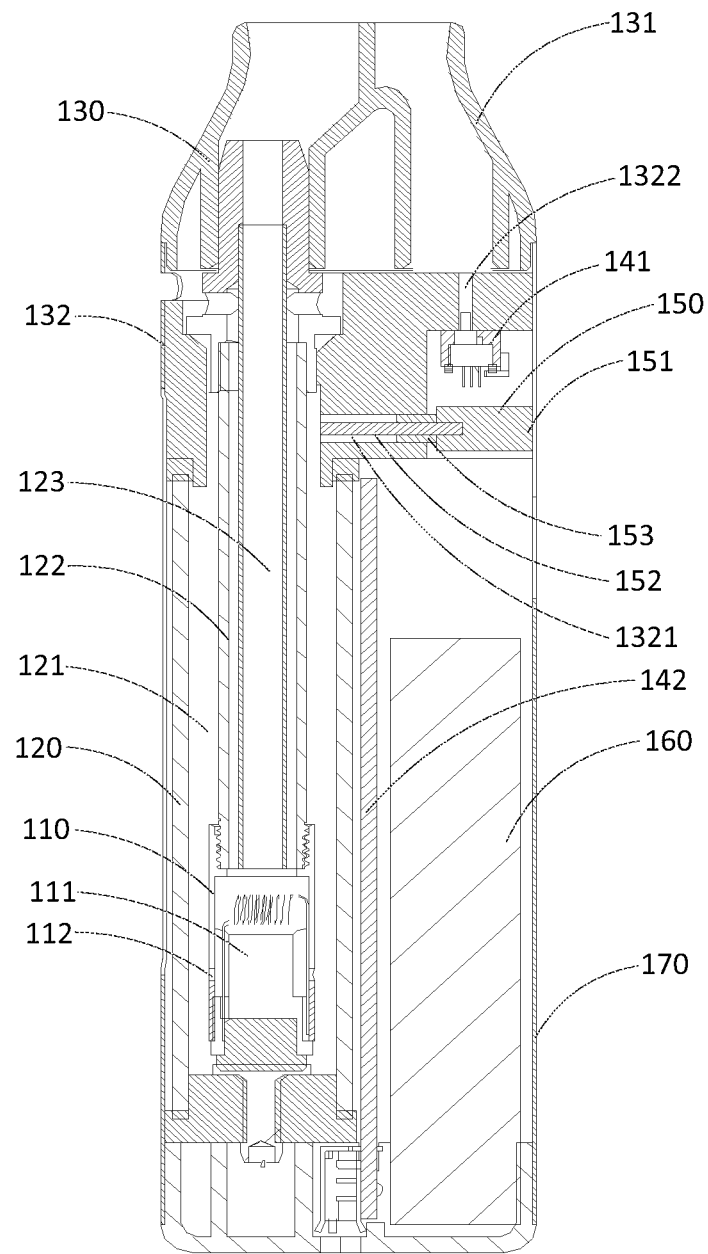
FIG. 3 is a cross-sectional view of an electronic cigarette according to the second embodiment of the present disclosure.
Figure 4:
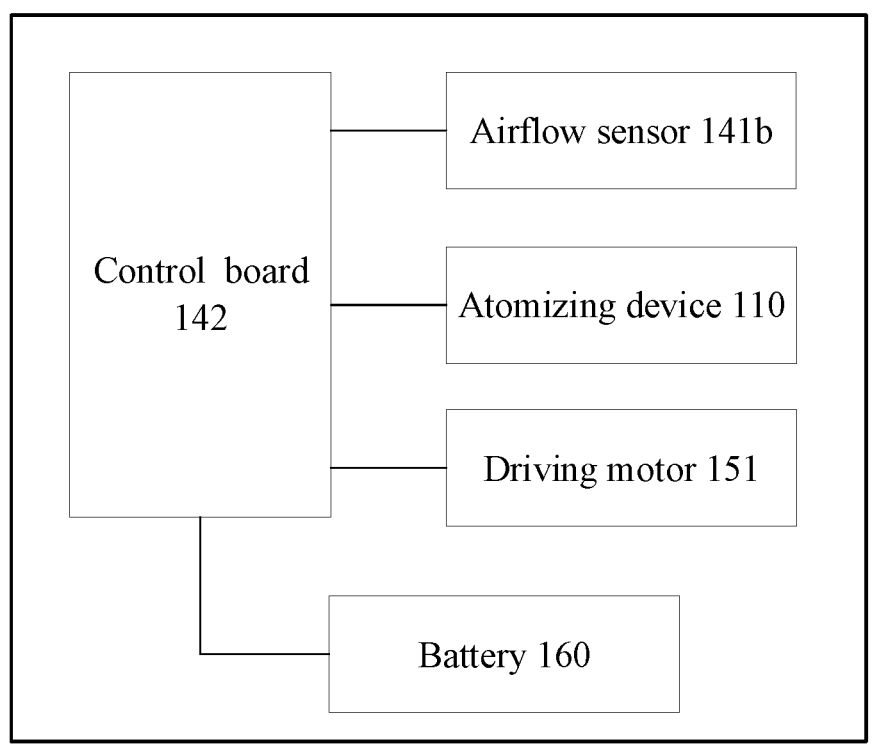
FIG. 4 is a block diagram of the second embodiment of the present disclosure.

Please refer to FIG. 3 and FIG. 4, the difference between the second embodiment and the first embodiment is as follows. In the embodiment, the control switch 141 is an airflow sensor 141b, an airflow detecting channel 1322 in communication with the mouthpiece 131 is defined in the mouthpiece connector 132, the airflow sensor 141b is located in the airflow detecting channel 1322. The airflow sensor 141b can detect the velocity of the airflow in the airflow detecting channel 1322 when the user smokes. A corresponding relationship between the rotational speed of the driving motor 151 and the flow velocity of the airflow is preset in the control board 142. It should be noted that, when the airflow sensor 141b detects the airflow, the atomizing device 110 is triggered, the control board 232 controls the rotational speed of the driving motor 151 based on the flow velocity detected by the airflow sensor 141b to control the liquid intake amount.

It can be understood that, as long as the detection of the flow velocity in the electronic cigarette can be achieved, the airflow sensor 141b can also be disposed at other positions of the electronic cigarette, such as in the gap between the vent pipe 122 and the air outlet pipe 123, or at the air inlet hole 133 of the electronic cigarette.

In this embodiment, when the electronic cigarette is in use, the user inhales the electronic cigarette, the airflow sensor 141b detects the airflow in the airflow detecting channel 1322. While the atomizing device 110 is turned on, the data of the airflow velocity is sent to the control board 142 and the control board 142 is triggered. Then, the control board 142 matches the data received from the airflow sensor 141b with the preset relationship between the rotational speed of the driving motor 151 and the air flow rate, and controls the driving motor 151 to rotate. In the initial state, the slider 153 stays on the side of the communication groove 1321 away from the liquid storage chamber 121. When the detected airflow rate is large, the atomizing device 110 generates a large amount of smoke, the driving motor 151 rotates faster, and the driving slider 153 moves rapidly toward the liquid storage chamber 121, the e-cigarette liquid in the liquid storage chamber 121 quickly enters the atomizing chamber 111, to satisfy the demand of the atomizing device 110 for the amount of e-cigarette liquid and avoid the occurrence of dry burning. When the detected airflow rate is small, the atomizing device 110 generates a small amount of smoke, the driving motor 151 has a low rotation speed or does not rotate, the driving slider 153 moves slowly or does not move in a direction close to the liquid storage chamber 121, and the e-cigarette liquid in the liquid storage chamber 121 slowly enters the atomizing chamber 111, which satisfies the requirement of the atomizing device 110 for the amount of e-cigarette liquid, avoids excessive e-cigarette liquid and insufficient atomization. At the end of the smoking, the driving motor 151 drives the slider 153 to move away from the liquid storage chamber 121, that is, the initial state is restored. At this time, the pressure in the liquid storage chamber 121 is reduced, the excess e-cigarette liquid in the atomizing chamber 111 returns to the liquid storage chamber 121 under the action of the air pressure, thereby avoiding the residual of the e-cigarette liquid in the atomizing chamber 111, reducing the possibility of leakage of e-cigarette liquid when the electronic cigarette is not used, and ensure that the user does not inhale the residual e-cigarette liquid when the user smokes again, ensuring the taste of smoking.

The Third Embodiment

Figure 5:
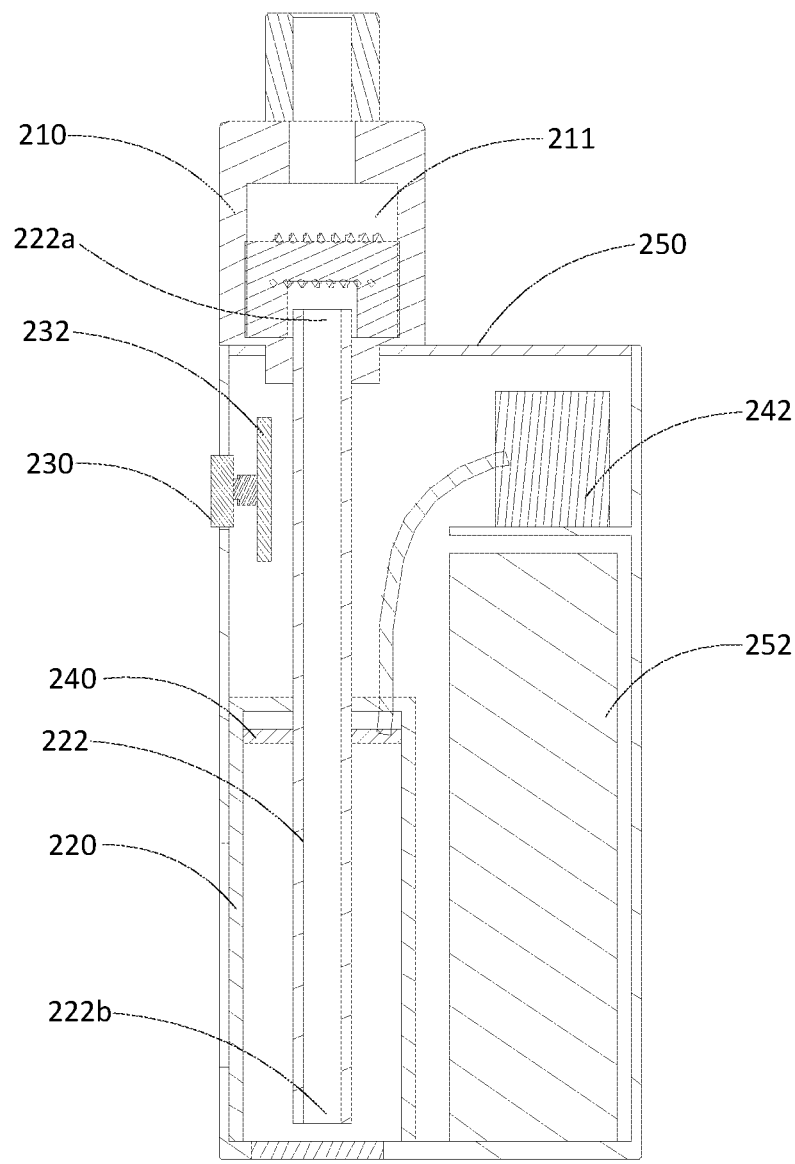
FIG. 5 is a cross-sectional view of an electronic cigarette according to the third embodiment of the present disclosure, in which the driving mechanism is simplified.
Figure 6:
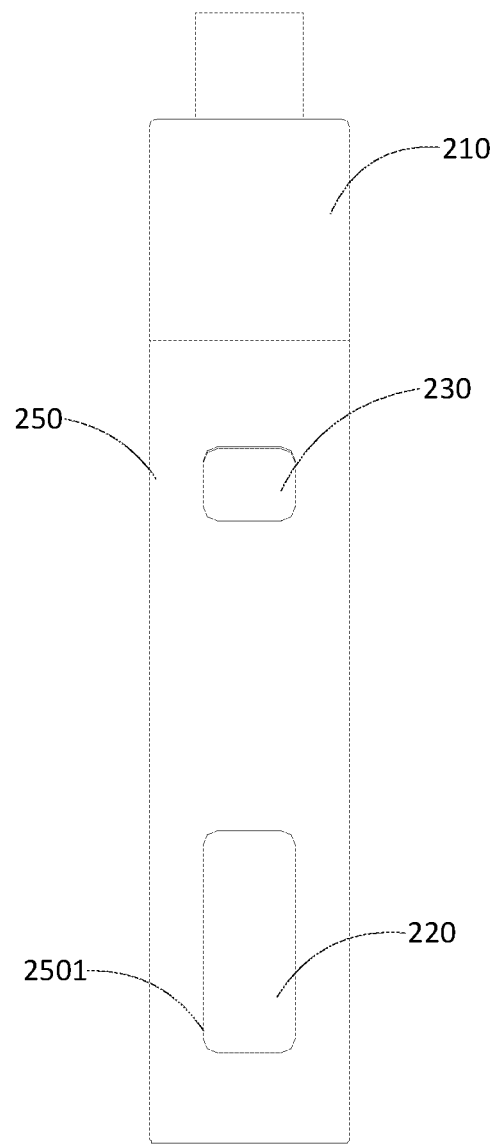
FIG. 6 is a right side view of the electronic cigarette shown in FIG. 5.
Figure 7:
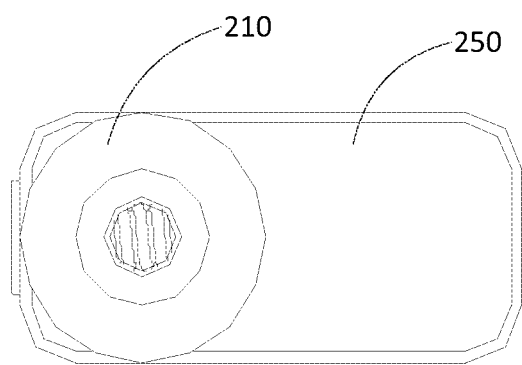
FIG. 7 is a top view of the electronic cigarette shown in FIG. 5.

Referring to FIG. 5 to FIG. 7, the electronic cigarette includes an atomizing device 210 and a liquid storage device. The atomizing device 210 includes an atomizing chamber 211. The electronic cigarette further includes a controller and a driving mechanism. The controller controls the supply of e-cigarette liquid of the electronic cigarette, the liquid storage device includes a liquid inlet tube 222 and a liquid storage chamber 220. A first end 222a of the liquid inlet tube 222 is in communication with the atomizing chamber 211, a second end 222b of the liquid inlet tube 222 is in communication with the liquid storage chamber 220, the driving mechanism is electrically connected to the controller and is controlled by the controller. When the controller controls the liquid intake of the electronic cigarette, the controller controls the driving mechanism to drive the e-cigarette liquid in the liquid storage chamber 220 to enter the atomizing chamber 211 through the liquid inlet tube 222. As long as the controller controls the supply of liquid of the electronic cigarette, the driving mechanism drives the e-cigarette liquid in the liquid storage chamber 220 to enter the atomizing chamber 211 through the liquid inlet tube 222, thereby ensuring that there is an appropriate amount of e-cigarette liquid in the atomizing chamber 211, and dry burning does not occur. Therefore, the present disclosure can effectively solve the dry burning problem of the electronic cigarette. At the same time, the amount of e-cigarette liquid entering the atomizing chamber 211 through the liquid inlet tube 222 is controlled by the driving mechanism, the movement of the driving mechanism is controlled by the controller. Thus, the amount of the liquid entering the atomizing chamber 211 can be controlled by the controller, there is no risk of liquid leakage due to infiltration of more e-cigarette liquid on the liquid guiding element than consumption in the prior art. Therefore, the present disclosure can also solve the problem of leakage of electronic cigarettes.

The controller includes a control board 232, a liquid inlet control switch 230 and/or a liquid injection control switch, the liquid inlet control switch 230 and/or the liquid injection control switch are signally connected to the control board 232, the driving mechanism is controlled by the control board 232. When the liquid inlet control switch 230 or the liquid injection control switch is turned on, the control board 232 is triggered, and the control board 232 controls the movement of the driving mechanism. It should be noted that, in one embodiment, when the controller includes the liquid inlet control switch 230 and the control board 232, that is, the liquid injection control switch is not included, the liquid inlet control switch 230 is signally connected to the control board 232, the driving mechanism is controlled by the control board 232. When the liquid inlet control switch 230 is turned on, the control board 232 is triggered and the control board 232 controls the movement of the driving mechanism.

In another embodiment, when the controller includes a liquid injection control switch and a control board 232, that is, the liquid inlet control switch 230 is not included, the liquid injection control switch is connected to the control board 232, the driving mechanism is controlled by the control board 232. When the liquid injection control switch is turned on, the control board 232 is triggered, and the control board 232 controls the movement of the driving mechanism.

It can be understood that, when the controller includes the control board 232, the liquid inlet control switch 230 and the liquid injection control switch, the liquid inlet control switch 230 and the liquid injection control switch are signally connected to the control board 232, the driving mechanism is controlled by the control board 232. When the liquid inlet control switch 230 or the liquid injection control switch is turned on, the control board 232 is triggered, and the control board 232 controls the movement of the driving mechanism.

Referring to FIG. 5, in the embodiment, the controller includes a liquid inlet control switch 230 and a control board 232. The liquid inlet control switch 230 is signally connected to the control board 232, the driving mechanism is coupled controlled by the control board 232. When the liquid inlet control switch 230 is turned on, the control board 232 is triggered. Since the driving mechanism is coupled controlled by the control board 232, the triggered control board 232 can control the movement of the driving mechanism. It can be understood that the control board 232 is provided with a chip, the amount of movement of the driving mechanism can be controlled by the chip, the amount of the e-cigarette liquid entering the atomizing chamber 211 can be set to realize the quantitative liquid introduction. It can be understood that, the liquid inlet control switch can be a mechanical physical button or a virtual button on the touch screen. For example, referring to FIG. 5, in the embodiment, the liquid inlet control switch is a mechanical physical button. In one embodiment not shown, the liquid inlet control switch can share the same switch as the switch that controls the atomization of the electronic cigarette, so that it is not necessary to separately set a liquid inlet control switch. When the atomization of the electronic cigarette is turned on, the liquid can be automatically started, that is, as long as the user is smoking the electronic cigarette, it is ensured that the atomizing chamber 211 has an appropriate amount of the e-cigarette liquid, so that the dry burning problem of the electronic cigarette can be completely avoided. In order to facilitate the control of the amount of liquid, the controller further includes a liquid intake amount control portion (not shown). The liquid amount controller is signally connected to the control board 232 for transmitting the information of the liquid intake amount control portion to the control board 232 for controlling the amount of e-cigarette liquid to be fed each time. The liquid intake amount control portion may be a mechanical physical button or a virtual button on the touch screen. For example, when the electronic cigarette adopts a mechanical liquid intake amount control portion, a plurality of gear positions can be set, and each gear position corresponds to the amount of liquid inlet each time. When the electronic cigarette adopts the touch screen type liquid intake amount control portion, the value of specific amount of liquid can be set on the touch screen and more flexibility.

Further, the controller further includes an atomization control switch (not shown). Press the atomization control switch, the electronic cigarette turns on the atomization, and the electronic cigarette can be started at this time. It can be understood that, the liquid inlet control switch 230 and the atomization control switch can be controlled separately or coupled controlled. When the liquid inlet control switch 230 is coupled controlled with the atomization control switch, that is, when the atomization control switch is turned on, the liquid inlet control switch is automatically turned on. That is, when the user smokes the electronic cigarette, the liquid enters the electronic cigarette automatically so that the dry burning problem can be completely avoided. It can be understood that, when the liquid inlet control switch 230 and the atomization control switch are separately controlled, the liquid inlet control switch 230 is first pressed to have an appropriate amount of e-cigarette liquid in the atomizing chamber 211, and then the atomization control switch is pressed for smoking.

It should be noted that, the driving mechanism is controlled by the control board 232, the driving mechanism and the control board 232 can be moved at almost the same time or can be delayed by a set time. For example, when the control board 232 is triggered, the driving mechanism is triggered almost simultaneously; or, the driving mechanism is triggered after a period of time after the control board 232 is triggered.

The driving mechanism includes a piston 240, a connecting member and a driving motor 242. The piston 240 is located in the liquid storage chamber 220. The piston 240 is similar to the piston of the hydraulic cylinder, and divides the liquid storage chamber 220 into a cavity 220b and a communication chamber 220a. The cavity 220b does not store the e-cigarette liquid. The communication chamber 220a is used for storing the e-cigarette liquid, the communication chamber 220a is in communication with the atomizing chamber 211 through the liquid inlet tube 222. The connecting member is connected between the piston 240 and the driving motor 242. When the piston 240 moves toward the communication chamber 220a, the volume of the communication chamber 220a is compressed, the e-cigarette liquid can be squeezed into the liquid inlet tube 222 and enter the atomizing chamber 211 via the liquid inlet tube 222.

Figure 8:
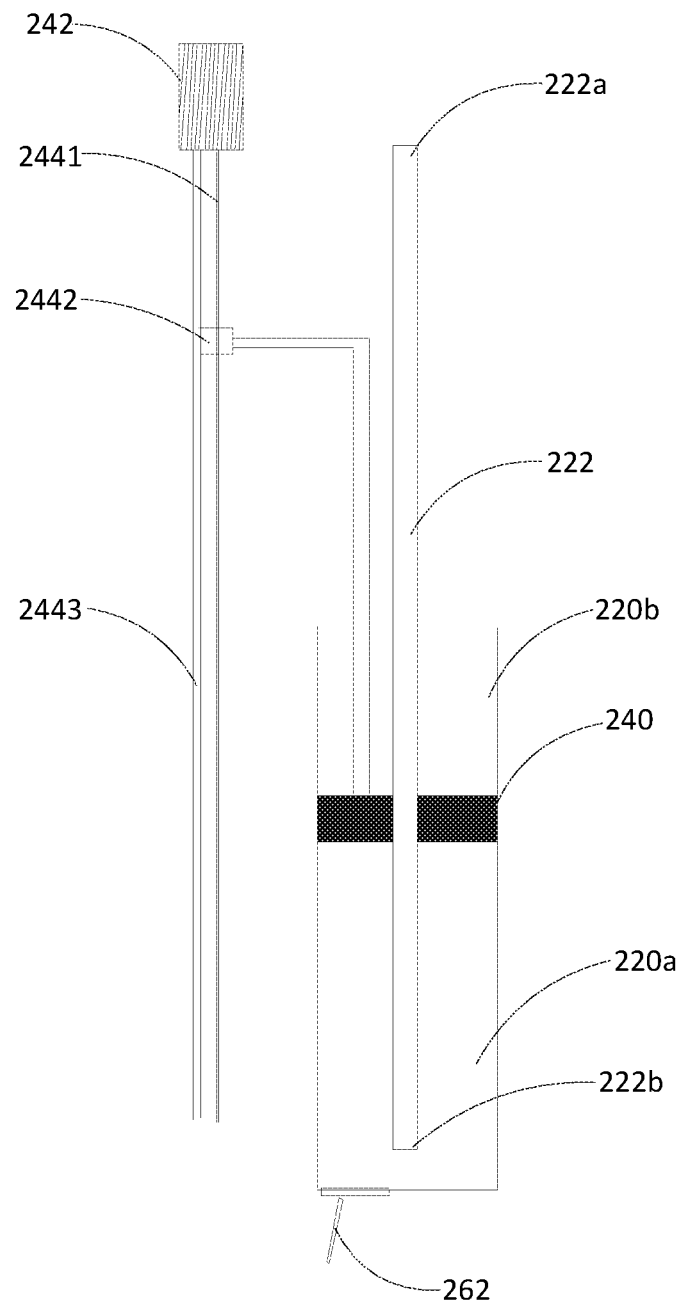
FIG. 8 is a schematic view of the driving mechanism and a liquid storage device according to the third embodiment of the present disclosure.
Figure 9:
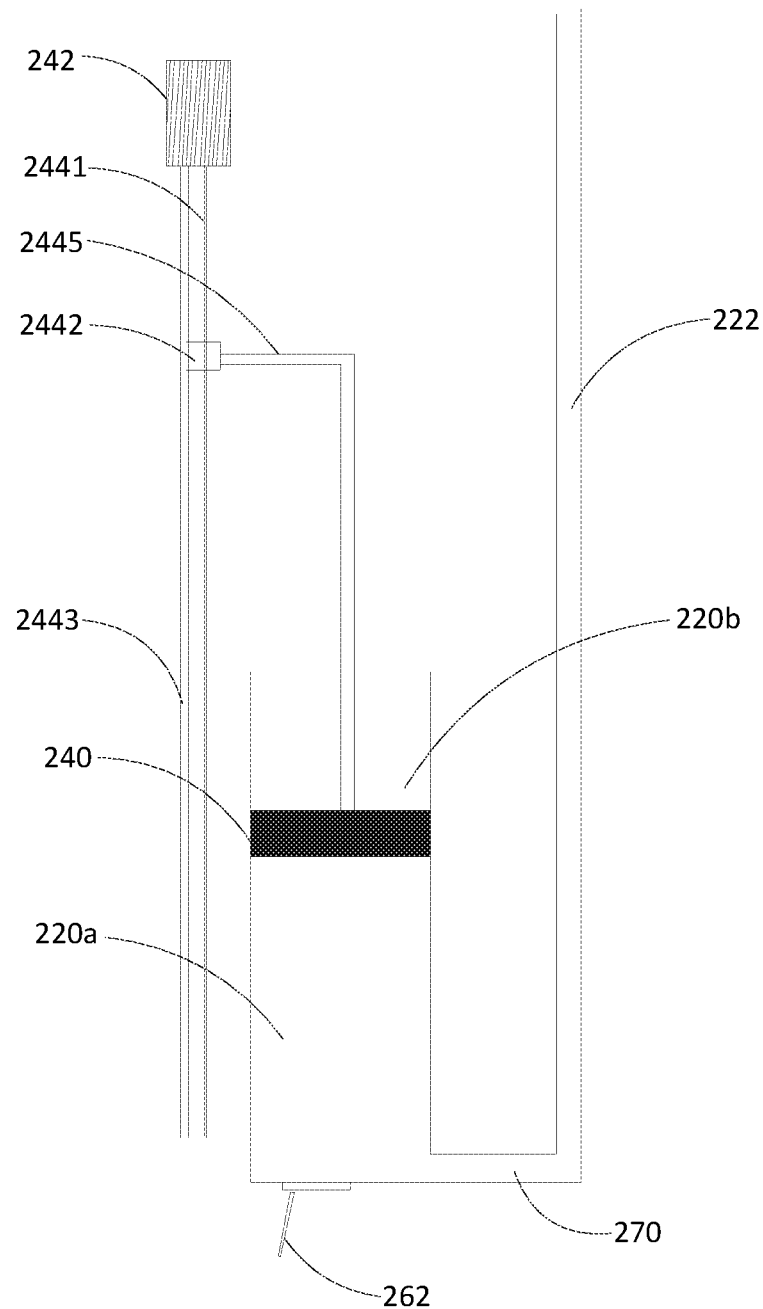
FIG. 9 is another schematic view of the driving mechanism and a liquid storage device according to the third embodiment of the present disclosure.

The connecting member is for converting a rotational motion of the driving motor 242 into a linear motion of the piston 240. Referring to FIG. 8 and FIG. 9, the connecting member includes a screw rod 2441, a slider 2442, a guide rail 2443 and a connecting rod 2445. The lead screw rod 2441 is connected to the driving motor 242, the driving motor 242 drives the screw rod 2441 to rotate. The screw rod 2441 extends through the slider 2442, the slider 2442 is slidably connected to the guide rail 2443. The connecting member converts the rotational motion of the driving motor 242 into a linear motion of the slider 2442. One end of the connecting rod 2445 is fixedly connected to the slider 2442, and the other end of the connecting rod 2445 is fixedly connected to the piston 240. Therefore, when the slider 2442 is linearly moved, the piston 240 can be driven to perform linear motion therewith. With the screw rod structure, a precise metering liquid supply can be achieved. The rotation of the screw rod 2441 can realize a linear movement of the piston 240 for a certain distance, so that a certain amount of e-cigarette liquid can be supplied. The rotation of the driving motor 242 can be controlled by the control board 232, thereby achieving control the amount of movement of the piston 240, and the quantitative liquid feeding of the e-cigarette liquid can be realized.

The driving motor 242 of the present disclosure can employ any form of motor, when the driving motor 242 is a stepper motor or a servo motor, the movement of the piston 240 can be more precisely controlled.

As long as the rotational motion of the driving motor 242 can be converted into a linear motion of the piston 240, the connecting member can take any other form. For example, in an embodiment not shown, the connecting member is a rack and piston structure, that is, a gear is fixedly connected to an output shaft of the driving motor 242, and an upper end of the rack is engaged with the gear, the lower end of the rack is fixedly connected to the piston 240. The piston 240 moves linearly under the drive of the rack.

The connection position of the liquid inlet tube 222 and the liquid storage chamber 220 is not limited. For example, referring to FIG. 8, in one embodiment, the second end 222b of the liquid inlet tube 222 passes through the cavity 220b and the piston 240 in sequence, the second end 222b of the liquid inlet tube 222 is inserted into the communication chamber 220a. The e-cigarette liquid in the communication chamber 220a can be injected into the liquid inlet tube 222 as the piston 240 moves from the cavity 220b toward the communication chamber 220a. Further, the second end 222b of the liquid inlet tube 222 is close to the bottom of the communication chamber 220a, so that the e-cigarette liquid can be injected into the liquid inlet tube 222 even when the amount of e-cigarette liquid in the communication chamber 220a is small.

Referring to FIG. 9, in another embodiment, the liquid storage device further includes a connecting tube 270 disposed between the communication chamber 220a and the liquid inlet tube 222. The communication chamber 220a is in communication with the liquid inlet tube 222 through the connecting tube 270, that is, the liquid inlet tube 222 no longer passes through the cavity 220b, but a through hole is formed in the wall of the communication chamber 220a, the connection tube 270 is connected to the through hole. Further, the through hole corresponding to the connecting tube 270 is close to the bottom of the communication chamber 220a, so that the e-cigarette liquid can be squeezed into the liquid inlet tube 222 even when the amount of e-cigarette liquid in the communication chamber 220a is small.

Referring to FIG. 5, the electronic cigarette further includes a battery device and a housing 250. The battery device includes a battery 252, the battery 252 is located in the housing 250. In this embodiment, the liquid storage device and the driving mechanism are both disposed in the housing 250. That is, the liquid storage device, the driving mechanism and the battery 252 share the same housing 250, the atomizing device 210 is disposed above the housing 250, such that the atomizing device 210 can be connected to the housing 250 to complete the connection between the atomizing device 210, the battery device and the liquid storage device. In another embodiment (not shown) the atomizing device 210, the liquid storage device and the driving mechanism are disposed within the housing 250.

In order to avoid liquid leakage, the portion of the piston 240 that is in contact with the inside of the liquid storage chamber 220 is provided with a sealing ring, that is, the piston 240 and liquid storage chamber 220 are sealed connection through the sealing ring. Therefore, the cavity 220b can be either closed or open-ended.

Referring to FIG. 6, in order to facilitate observation of the amount of e-cigarette liquid in the liquid storage chamber 220, the peripheral wall of the liquid storage chamber 220 can be made of a transparent material such as glass, transparent resin, etc., and an observation window 2501 is disposed on the housing 250. The amount of e-cigarette liquid in the liquid storage chamber 220 can be visually observed through the observation window 2501. It can be understood that, the material of the peripheral wall of the liquid storage chamber 220 can also be selected as a non-transparent material. In this case, a liquid level detecting device can be disposed in the liquid storage chamber 220, and the electronic cigarette is provided with a display screen correspondingly. The liquid level detecting device is electrically connected to the display screen for transmitting the liquid level information detected by the liquid level detecting device to the user through the display screen, thereby obtaining the amount of the e-cigarette liquid through the liquid level detecting device. It can be understood that, when the electronic cigarette adopts the display touch screen, the display touch screen is the display screen.

Figure 10:
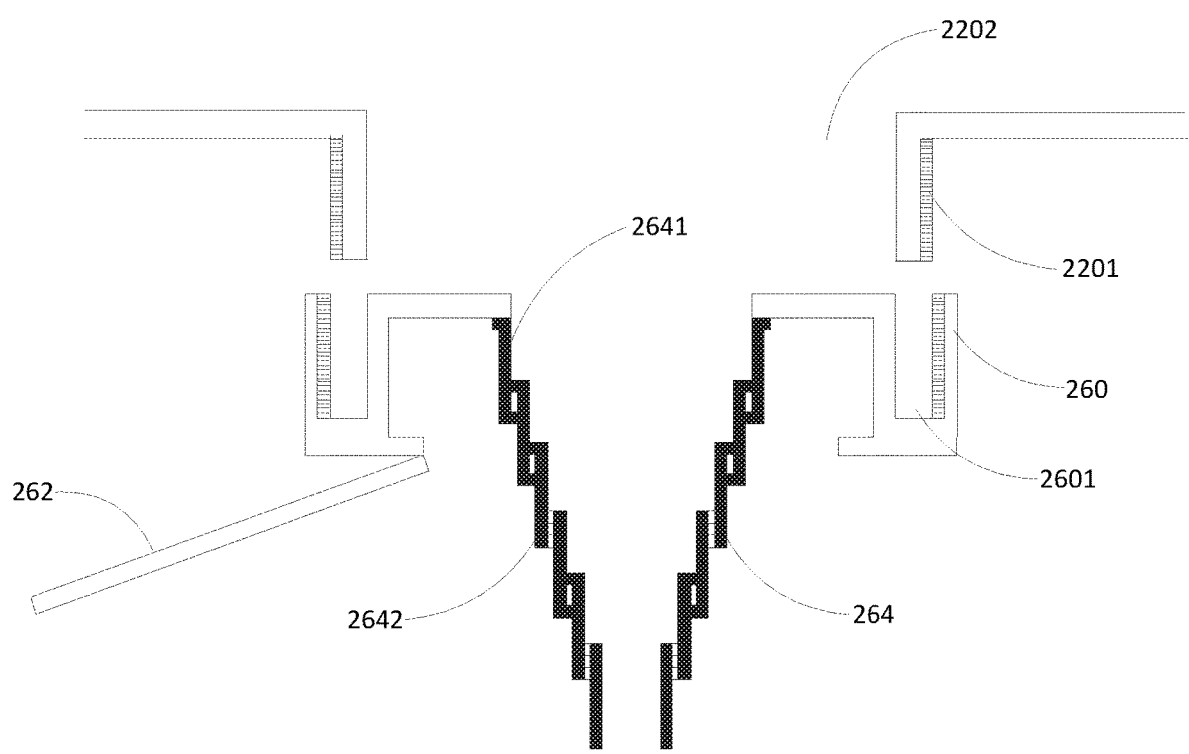
FIG. 10 is a schematic view of a liquid injection device according to the third embodiment of the present disclosure.

Referring to FIG. 10, an injection hole 2202 is defined at the bottom of the liquid storage chamber 220. An opening is provided at the bottom wall of the housing 250 corresponding to the injection hole 2202, so that the liquid storage chamber 220 can be replenished with the e-cigarette liquid through the opening and the injection hole 2202. The electronic cigarette further includes a liquid injection assembly for covering the opening, the liquid injection assembly includes a mounting member 260, an opening and closing member 262, and a telescopic liquid injection tube 264. The telescopic liquid injection tube 264 can be extended or shortened, the telescopic liquid injection tube 264 is fixedly connected to the mounting member 260, the opening and closing member 262 is rotatably connected to the mounting member 260. The mounting member 260 is connected to the bottom wall of the housing 250, that is, the liquid injection assembly is connected to the bottom wall of the housing 250 through the mounting member 260. The upper port of the telescopic liquid injection tube 264 is sealing connected to the opening. The opening and closing member 262 includes an open state and a closed state. When the opening and closing member 262 is in the closed state, the lower port of the telescopic liquid injection tube 264 is sealing abutted against the opening and closing member 262. That is, when the opening and closing member 262 is in the closed state, the opening and closing member 262 blocks the lower port of the telescopic liquid injection tube 264, thereby blocking the liquid storage chamber 220, so that the e-cigarette liquid in the liquid storage chamber 220 does not leak through the liquid injection hole 2202. In order to facilitate the control of the liquid injection process, the controller further includes a liquid injection control switch (not shown), pressing the liquid injection control switch, the electronic cigarette can start to inject liquid. It can be understood that, the liquid injection switch can be a mechanical physical button or a virtual button on the touch screen. Further, to facilitate the control of the amount of liquid injection, the controller further includes a liquid injection amount control portion for setting and controlling the amount of liquid injection each time. For example, when the electronic cigarette adopts the mechanical liquid injection amount control portion, a plurality of gear positions can be set, each gear position corresponds to the amount of liquid injection each time. When the electronic cigarette adopts the touch screen typed liquid injection amount control portion, a specific liquid injection amount value can be set on the touch screen and more flexibility.

The liquid injection control switch and the liquid inlet control switch can be separate switches or a common switch, the two modes of infusion or infusion are switched by chip control in the control panel.

The telescopic liquid injection tube 264 includes a first tube 2641 and a multiple telescopic tubes 2642. The first tube 2641 is fixedly connected to the mounting member 260, the two adjacent telescopic tubes 2642 are nested and connected, the telescopic tube 2642 of the next section is not removed from the upper telescoping tube 2642. The structure of the telescopic liquid injection tube 264 is similar to that of the engineering crane, and will not be described herein. Opening the opening and closing member 262 (the opening and closing member 262 is in the opened state), each telescopic tube 2642 is automatically extended under the action of its own gravity. At this time, the telescopic liquid injection tube 264 can be inserted into the liquid bottle, the driving motor 242 is controlled to be reversed by the controller to drive the piston 240 to move toward the cavity 220b (i.e., the piston 240 moves upward) to achieve automatic liquid injection. When the automatic injection is required, the opening and closing member 262 is operated to be in an open state, the telescopic liquid injection tube 264 is extended by gravity, the lower end of the telescopic liquid injection tube 264 is inserted into the liquid bottle. At this time, clicking the liquid injection control switch or the liquid inlet control switch (when the liquid inlet control switch and the liquid injection control switch share the same switch), the automatic liquid injection is started. In addition, the amount of rotation of the driving motor 242 can also be set by the controller, thereby controlling the movement stroke of the piston 240 to achieve quantitative liquid injection. Unscrew the lower cover and set up the electronic cigarette, can directly pour the liquid into the liquid storage chamber 220, but this cannot accurately control the injection amount. Further, a single-conducting portion (not shown) is disposed in the liquid inlet tube 222, the single-conducting portion allows the liquid in the liquid storage chamber 220 to enter the atomizing chamber 211 in one direction. It can be understood that, the one-way through portion can also be disposed in the connecting tube 270. The single-conducting portion prevents the e-cigarette liquid in the atomizing chamber 211 from flowing back into the liquid storage chamber 220 when the liquid is injected into the liquid storage chamber 220 through the liquid injection assembly. It can be understood that, the one-way passage can be a one-way valve or a one-way membrane.

Furthermore, the injection hole 2202 at the bottom of the liquid storage chamber 220 has a convex ring 2201 protruding outward. The mounting member 260 is provided with a groove 2601 for engaging with the convex ring 2201. The convex ring 2201 is embedded in the groove 2601, the liquid storage chamber 220 and the mounting member 260 are detachably connected by the convex ring 2201 and the groove 2601. There are many ways to achieve detachable connection, such as snap connection and threaded connection. In the embodiment, a threaded connection is used. Specifically, referring to FIG. 10, the convex ring 2201 is provided with an external thread, the groove 2601 is provided with an internal thread, the convex ring 2201 is screwed connected to the groove 2601. The center of the mounting member 260 has a through hole corresponding to the liquid injection hole 2202. The upper end of the telescopic liquid injection tube 264 is fixedly connected to the mounting member 260, the upper port of the telescopic liquid injection tube 264 corresponds to the through hole of the mounting member 260. The telescopic liquid injection tube 264 communicates with the liquid storage chamber 220 through the through hole.

Although the description has been made in accordance with the embodiments of the present disclosure as described above, it will be understood by those skilled in the art that the various embodiments of the present disclosure described above may be made without departing from the scope of the disclosure. Improvements. Therefore, the scope of the disclosure should be determined by the content of the appended claims

What is claimed is:

1. An electronic cigarette, comprising:
a liquid storage device comprising a liquid storage chamber;
an atomizing device comprising an atomizing chamber;
a controller; and
a driving mechanism,
wherein the driving mechanism is electrically connected to the controller, and, during operation, the controller controls the liquid intake of the electronic cigarette by controlling the driving mechanism to drive the e-cigarette liquid in the liquid storage chamber to enter the atomizing chamber,
wherein the electronic cigarette further comprises a housing, the liquid storage chamber is located in the housing, a liquid inlet is defined at the bottom of the liquid storage chamber, an opening is provided at the bottom wall of the housing corresponding to the liquid inlet,
wherein the electronic cigarette further comprises a liquid injection assembly for covering the opening,
wherein the liquid injection assembly comprises a mounting member, an opening and closing member, and a telescopic liquid filling tube fixedly connected to the mounting member, the opening and closing member is rotatably connected to the mounting member, the mounting member is connected to the housing, the upper port of the telescopic infusion tube is sealing connected to the opening, the opening and closing member has an open state and a closed state, when the opening and closing member is in the closed state, the lower port of the telescopic liquid filling tube is sealing abutted against the opening and closing member.

2. The electronic cigarette according to claim 1, wherein the controller controls the driving mechanism to drive the e-cigarette liquid remaining in the atomization chamber to return to the liquid storage chamber at the end of operation.

3. The electronic cigarette according to claim 1, wherein the electronic cigarette further comprises a communication groove in communication with the liquid storage chamber, the atomizing device further comprises an a liquid inlet, the atomizing chamber is in communication with liquid storage chamber through the liquid inlet,
wherein the driving mechanism comprises a driving motor, a screw rod and a slider, the screw rod and the slider are disposed in the communication groove, the driving motor is disposed on the side of the communication groove away from the liquid storage chamber, the slider is connected to the screw rod, and
wherein the lead screw is driven by the driving motor to drive the slider in a direction close to the liquid storage chamber or in a direction away from the liquid storage chamber.

4. The electronic cigarette according to claim 3, wherein the slider is slidably connected to the screw rodfill, and, when the driving motor rotates, the screw rod is driven to rotate and drives slider to slide in a direction close to the liquid storage chamber or to slide away from the liquid storage chamber; or, the slider is disposed at one end of the screw rod near the liquid storage chamber, the screw rod is driven by the driving motor to make a telescopic motion and drives the slider to move in the direction close to or away from the liquid storage chamber in the communication groove.

5. The electronic cigarette according to claim 3, wherein the controller comprises a control switch and a control board, the control switch is signally connected to the control board, the driving mechanism is electrically connected to the control board and controlled by the control board, the controller further comprises an input device, the input device is signally connected to the control board, the input device is configured for inputting desired operating temperature, operating power, and/or operating voltage to the control board, the input device is a touch display or a touch switch.

6. The electronic cigarette according to claim 3, wherein the controller comprises a control switch and a control board, the control switch is signally connected to the control board, the driving mechanism is electrically connected to the control board and controlled by the control board, the control switch is an airflow sensor configured to detect the flow velocity of the airflow when the user smoking.

7. The electronic cigarette according to claim 1, wherein the liquid storage device includes a liquid inlet tube, a first end of the liquid inlet tube is in communication with the atomizing chamber, a second end of the liquid inlet tube is in communication with the liquid storage chamber, the controller controls the driving mechanism to drive the e-cigarette liquid in the liquid storage chamber into the atomization chamber through the liquid inlet tube.

8. The electronic cigarette according to claim 7, wherein the driving mechanism comprises a piston, a connecting member, and a driving motor, the piston is located in the liquid storage chamber and divides the liquid storage chamber into a cavity and a communication chamber, wherein the communication chamber is in communication with the atomizing chamber through the liquid inlet tube, the connecting member is connected between the piston and the driving motor and is configured to drive the piston to move toward the communication chamber.

9. The electronic cigarette according to claim 8, wherein the second end of liquid inlet tube passes through the cavity and the piston in sequence, and the second end of the inlet tube is inserted into the communication chamber.

10. The electronic cigarette according to claim 8, wherein the liquid storage device further comprises a connecting tube disposed between the communication chamber and the liquid inlet tube, and the communication chamber is in communication with the liquid inlet tube through the connecting tube.

11. The electronic cigarette according to claim 8, wherein the connecting member includes a screw, a slider, a rail, and a connecting rod, wherein the lead screw is connected to the driving motor, the screw rod extends through the slider, the slider is slidably connected to the guide rail, one end of the connecting rod is fixedly connected to the slider, and the other end of the connecting rod is fixedly connected to the piston.

12. The electronic cigarette according to claim 7, wherein the electronic cigarette comprises a liquid level detecting device disposed in the liquid storage chamber, the electronic cigarette further comprises a display screen, and the liquid level detecting device is electrically connected to the display screen.

13. The electronic cigarette according to claim 1, wherein, when the liquid inlet is in communication with a liquid bottle, the drive motor is controlled to be reversed by the controller, the connecting member drives the piston to move toward the cavity to achieve automatic liquid injection.

14. The electronic cigarette according to claim 1, wherein the telescopic liquid injection tube comprises a first tube and a multi-section telescopic tube, wherein the first tube is fixedly connected to the mounting member, and the two adjacent telescopic tubes are nested and connected.

15. The electronic cigarette according to claim 1, wherein a single-conducting portion is located in the liquid inlet tube, and is configured to prevent the e-cigarette liquid in the atomizing chamber from flowing back into the liquid storage chamber when the e-cigarette liquid is injected into the liquid storage chamber.

16. The electronic cigarette according to claim 1, wherein the controller includes a control board, a liquid inlet control switch and/or a liquid injection control switch, the liquid inlet control switch and/or the liquid injection control switch are signally connected to the control board, the driving mechanism is coupled controlled by the control board, and, when the liquid inlet control switch or the liquid injection control switch is turned on, the control board is triggered and the control board controls the movement of the driving mechanism.

17. The electronic cigarette according to claim 1, wherein the controller further comprises a liquid injection amount control portion and/or a liquid intake amount control portion, the liquid injection amount control portion and/or liquid intake amount control portion is signally connected to the control board, the liquid injection amount control portion comprises a plurality of gear positions, each gear position corresponds to the amount of liquid injection each time; or, the liquid injection amount control portion is a touch screen typed liquid injection amount control portion, the touch screen typed injection amount control portion is configured to set liquid injection amount value.

18. The electronic cigarette according to claim 1, wherein the controller further comprises an atomization control switch, the liquid inlet control switch, and the atomization control switch is controlled separately or coupled controlled.

\* \* \* \* \*